United States Patent [19]

Lopez

[11] Patent Number: 5,308,830
[45] Date of Patent: May 3, 1994

[54] TRIAZOLECARBOXAMIDE HERBICIDES

[75] Inventor: R. C. Gerardo Lopez, Doylestown, Pa.

[73] Assignee: Rohm and Haas Company, Philadelphia, Pa.

[21] Appl. No.: 385,858

[22] Filed: Jul. 26, 1989

Related U.S. Application Data

[63] Continuation of Ser. No. 115,127, Oct. 30, 1987, abandoned, which is a continuation of Ser. No. 733,158, May 13, 1985, abandoned.

[51] Int. Cl.$^5$ .................. A01N 43/653; C07D 249/12
[52] U.S. Cl. .................. 504/273; 548/264.2; 548/264.4
[58] Field of Search ............ 548/265, 264.2, 264.4; 71/92; 504/273

[56] References Cited

U.S. PATENT DOCUMENTS 4,251,262 2/1981 Brookes et al. .................. 548/265
4,702,764 10/1987 Nakayama et al. .................. 548/265

Primary Examiner—Patricia L. Morris
Attorney, Agent, or Firm—Terence P. Strobaugh; Michael B. Fein

[57] ABSTRACT

Compounds of the formula:

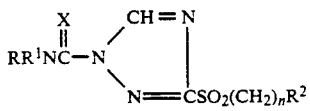

wherein X is O or S; R and $R^1$ are substituted or unsubstituted alkyl, alkenyl, alkynyl or cycloalkyl or R and $R^1$ may be joined to form a heterocyclic ring; $R^2$ is substituted or unsubstituted cycloalkyl; and n is 0, 1 or 2 are disclosed as well as their postemergence and preemergence selective herbicide use against both monocot and dicot weeds in crops such as sugarbeets, cotton, soybeans and rice.

13 Claims, No Drawings

TRIAZOLECARBOXAMIDE HERBICIDES

This application is a continuation of application Ser. No. 07/115,127, filed Oct. 30, 1987, now abandoned, which is a continuation of application Ser. No. 733,158 filed May 13, 1985, now abandoned.

Description of the Invention

The search for selective herbicides which will adversely affect weeds but not crops is a continuing one. Also, the search for herbicides effective at low doses is continuing because lower doses will have lower residues and be less of a negative environmental impact.

I have discovered that compounds of the formula:

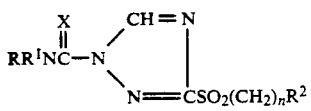

wherein X is O or S; R and $R^1$ are substituted or unsubstituted alkyl, for example, lower alkyl of from 1 to 6 carbon atoms such as methyl, ethyl, propyl, butyl, pentyl, hexyl and, where possible, isomers thereof; substituted or unsubstituted alkenyl, for example lower alkenyl of from 2 to 6 carbon atoms such as vinyl, allyl, butenyl, pentenyl, hexenyl and, where possible, isomers thereof; alkynyl, for example, lower alkynyl of from 2 to 6 carbon atoms such as ethynyl, propynyl, butynyl, pentynyl, hexynyl and where possible isomers thereof, wherein the substituent is selected from lower alkoxy of from 1 to 6 carbon atoms such as methoxy, ethoxy and the like, or halo such as bromo, chloro and the like or substituted or unsubstituted cycloalkyl, for example, cycloalkyl of from 3 to 6 carbon atoms such as cyclopropyl, cyclobutyl or cyclopentyl wherein the substituent is selected from lower alkyl, lower alkenyl, lower alkynyl, lower alkoxy lower alkyl or halo; R and $R^1$ may be joined together with the nitrogen to which these are attached to form a heterocyclic ring of from 2 to 6 nuclear carbon atoms containing 1 or 2 hetero atoms selected from oxygen and nitrogen such as pyrrolidino, piperidino, morpholino, piperazino, methylpiperazino, dimethylpyrrolidino, dimethylpiperidino, dimethylmorpholino, dimethylpiperazino, hexamethyleneimino; $R^2$ is substituted or unsubstituted cycloalkyl, for example, cycloalkyl of from 3 to 9 nuclear carbon atoms such as cyclopropyl, cyclobutyl, cyclopentyl, cyclohexyl, cycloheptyl, cyclooctyl, cyclononyl and the like, wherein the substituent can be from 1 to 4 radicals selected from lower alkyl, lower alkenyl, lower alkynyl, lower alkoxy lower alkyl, halo lower alkyl, halo lower alkenyl, halo lower alkynyl, cyano or halo and n is 0, 1 or 2.

Preferred compounds are those of the formula:

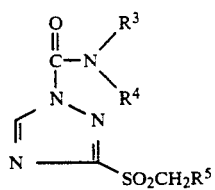

where $R^3$ and $R^4$ are the same or different lower alkyl or lower alkenyl radicals and $R^5$ is cycloalkyl of from 3 to 7 nuclear carbon atoms.

The products of this invention can be prepared by several alternative processes. One process comprises treating a compound of the formula:

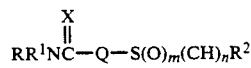

wherein R, $R^1$, $R^2$, X and n are as defined above,

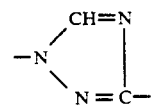

and m is 0 or 1 with an oxidizing agent, for example, a peroxide such as hydrogen peroxide and the like. This reaction is conducted at a temperature in the range of from about 0° to about 120° C.

Another process for preparing the compounds of this invention comprises treating a compound of the formula:

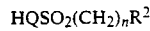

where $R^2$, Q and n are as defined above with a compound of the formula:

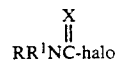

wherein R, $R^1$ and X are as defined above and halo is chloro, bromo and the like.

The following flow diagram illustrates two methods for the preparation of the starting materials, intermediates and final products.

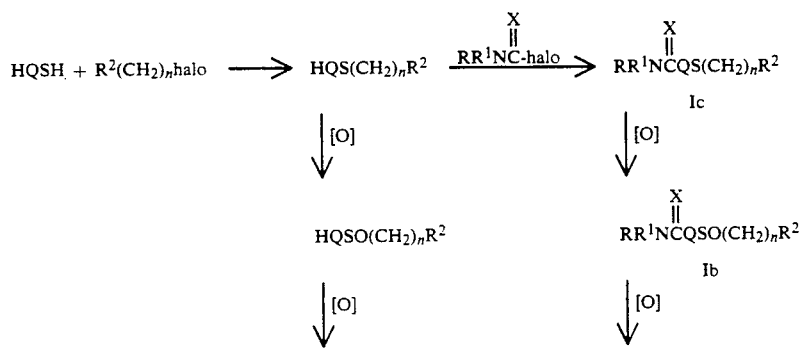

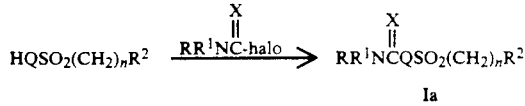

Ia

The triazolecarboxamides of the invention are useful as preemergence and postemergence selective herbicides. Preemergence herbicides are used to treat the soil by application either before seeding, during seeding, or after seeding and before the crop emerges. Postemergence herbicides are those which are applied after the plants have emerged and during their growth period. The compounds of this invention are especially active as preemergence herbicides.

Among the crops on which the triazolecarboxamides of the invention can be advantageously employed are sugarbeets, cotton, soybeans, and rice.

The triazolecarboxamides are useful for controlling weeds in rice crops. When used in transplanted rice crops, the triazolecarboxamides can be applied either preemergence or postemergence to the weeds—that is, they can be applied to the transplanted rice plants and their growth medium either before the weed plants have emerged or while they are in their early stages of growth. The triazolecarboxamides can be applied to the growth medium either before or after the rice has been transplanted to that medium.

The triazolecarboxamides can be applied in any amount which will give the required control of weeds. A standard rate of application of the herbicides of the invention is in the range from about 0.02 to about 10 pounds per acre. A preferred range is from about 0.1 to about 2 pounds per acre.

Under some conditions, the triazolecarboxamides may be advantageously incorporated into the soil or other growth medium prior to planting a crop. This incorporation can be by any convenient means, including simple mixing with the soil, applying the carboxamide to the surface of the soil and then disking or dragging into the soil to the desired depth, or by employing a liquid carrier.

The products of the invention can be applied to the growth medium or to plants to be treated either neat or as a component in a herbicidal composition or formulation which also comprises an agronomically acceptable carrier. "Agronomically acceptable carrier" is any carrier which can be used to dissolve, disperse or diffuse a herbicidal compound in the composition without impairing the effectiveness of the herbicidal compound and which by itself has no permanent detrimental effect on the soil, equipment, crops, or agronomic environment. Mixtures of the triazolecarboxamides of the invention may also be used in any of these herbicidal formulations. The herbicidal compositions of the invention can be either solid or liquid formulations or solutions. For example, the triazolecarboxamides can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in postemergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers 1969 Annual."

Examples of solvents which are useful in the practice of this invention include alcohols, ketones, aromatic hydrocarbons, dimethyl formamide, dioxane, dimethyl sulfoxide, and the like. Mixtures of these solvents can also be used. The concentration of the solution can vary from about 2% to about 98% of active product with a preferred range being from about 25% to about 75%.

For the preparation of emulsifiable concentrates, the triazolecarboxamide can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually from about 10% to 60% and in flowable emulsion concentrates, can be as high as about 75%.

Wettable powders suitable for spraying can be prepared by admixing the triazolecarboxamide with a finely divided solid, such as clay, inorganic silicate and carbonate, and silicas and then incorporating wetting agents, sticking agents, and/or dispersing agents. The concentration of active ingredients in such formulations is usually in the range of from about 20% to about 98%, and, preferably, from about 40% to about 75%. A dispersing agent can constitute about 0.5% to about 3% of the composition, and a wetting agent can constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing from about 20% to about 80% of the active ingredient are commonly made nd are subsequently diluted to about 1% to about 10% use concentration.

Granular formulations can be prepared by impregnating a solid, such as granular fuller's earth, vermiculite, ground corn cobs, seed hulls, including bran or other grain-hulls, or similar material. A solution of one or more of the triazolecarboxamides in a volatile organic solvent can be sprayed or mixed with the granular solid and the solvent then removed by evaporation. The granular material can have any suitable size, with a preferable size range of from 16 to 60 mesh. The triazolecarboxamides will usually comprise from about 2 to about 15% of the granular formulation.

The triazolecarboxamides of the invention can also be mixed with fertilizers or fertilizing materials before their application. In one type of solid fertilizing composition in which the triazolecarboxamides can be used, particles of a fertilizer or fertilizing ingredients, such as ammonium sulfate, ammonium nitrate, or ammonium phosphate, can be coated with one or more of the carboxamides. The solid triazolecarboxamides and solid fertilizing material can also be admixed in mixing or blending equipment, or they can be incorporated with fertilizers in granular formulations. Any relative proportion of triazolecarboxamides and fertilizer can be used which is suitable for the crops and weeds to be treated. The triazolecarboxamide will commonly be from about 5% to about 25% of the fertilizing composition. These compositions provide fertilizing materials which promote the rapid growth of desired plants, and at the same time control the growth of undesired plants.

The triazolecarboxamides of the invention can be applied as herbicidal sprays by methods commonly employed, such as conventional high-gallonage hydraulic sprays, low-gallonage sprays, airblast spray, aerial sprays and dusts. For low volume applications a solution of the compound is usually used. The dilution and rate of application will usually depend upon such factors as the type of equipment employed, the method of application, the area to be treated and the type and stage of development of the weeds.

For some applications, it may be desirable to add one or more other herbicides to the triazolecarboxamides of the invention. Examples of other herbicides which can be incorporated to provide additional advantages and effectiveness include:

Carboxylic Acids and Salts and Ester Derivatives Thereof 2,3,6-trichlorobenzoic acid, 2,3,4,5-tetrachlorobenzoic acid, 2-methoxy-3,5,6-trichlorobenzoic acid, 2-methoxy-3,6-dichlorobenzoic acid, 2-methyl-3,6-dichlorobenzoic acid, 2,3-dichloro-6-methylbenzoic acid, 2,4,-dichlorophenoxyacetic acid, 2,4,5-trichlorophenoxyacetic acid, 2-methyl-4-chlorophenoxyacetic acid, 2-(2,4,5-trichlorophenoxy)propionic acid, 4-(2,4-dichlorophenoxy)-butyric acid, 4-(2-methyl-4-chlorophenoxy)butyric acid, 2,3,6-trichlorophenylacetic acid, 3,6-endoxohexahydrophthalic acid, dimethyl 2,3,5,6-tetrachloroterephthalate, trichloroacetic acid, 2,2,-dichloropropionic acid, 3-amino-2,5-dichlorobenzoic acid, 2,3-dichloroisobutyric acid.

Carbamic Acid Derivatives

Ethyl N,N-di(n-propyl)thiocarbamate, propyl N,N-di-(n-propyl)thiocarbamate, ethyl N-ethyl-N-(n-butyl)-thiocarbamate, ethyl N-ethyl-N-(n-butyl)thiocarbamate, propyl N-ethyl-N-(n-butyl)thiocarbamate, 2-chloroallyl N,N-diethyldithiocarbamate, N-methyldithiocarbamic acid salts, ethyl 1-hexamethyleneiminecarbothiolate, isopropyl N-phenylcarbamate, isopropyl N-(m-chlorophenyl)carbamate, 4-chloro-2-butynyl N-(m-chlorophenyl)carbamate, methyl N-(3,4-dichlorophenyl)carbamate, methyl-m-hydroxcarbanilate-m-methylcarbanilate, S-(4-chlorobenzyl)-N,N-diethylthiolcarbamate.

Phenols dinitro-o-(sec-butyl)phenol and its salts, pentachlorophenol and its salts.

Substituted Ureas 3-(3,4-dichlorophenyl)-1,1-dimethylurea, 3-phenyl-1,1-dimethylurea, 3-(3,4-dichlorophenyl)-3-methoxy-1,1-dimethylurea, 3-(4-chlorophenyl)-3-methoxy-1,1-dimethylurea, 3-(3,4-dichlorophenyl)-1-n-butyl-1-methylurea, 3-(3,4-dichlorophenyl)-1-methoxy-1-methylurea, 3-(4-chlorophenyl)-1-methoxy-1-methylurea, 3-(3,4-dichlorophenyl)-1,1,3-trimethylurea, 3-(3,4-dichlorophenyl)-1,1-diethylurea, dichloral urea, N'[4-[2-p-methylphenyl)ethoxy]phenyl]-N-methoxy-N-methylurea, 1,1,3-trimethyl-3-(5-p-chlorobenzylthio-1,3,4-thiadiazol-2-yl)urea, 3-[p-chlorophenoxy)phenyl]-1,1-dimethylurea.

Substituted Triazines 2-chloro-4,6-bis(ethylamino)-s-triazine, 2-chloro-4-ethylamino-6-isopropylamino-s-triazine, 2-chloro-4,6-bis(methoxypropylamino)-s-triazine, 2-methoxy-4,6-bis-(isopropylamino)-s-triazine, 2-chloro-4-ethylamino-6-(3-methoxypropylamino)-s-triazine, 2-methylmercapto-4,6-bis(ethylamino)-s-triazine, 2-methylmercapto-4-ethylamino-6-isopropylamino-s-triazine, 2-chloro-4,6-bis(isopropylamino)-s-triazine, 2-methoxy-4,6-bis(ethylamino)-s-triazine, 2-methoxy-4-ethylamino-6-isopropylamino-s-triazine, 2-methylmercapto-(2-methoxyethylamino)-6-isopropylamino-s-triazine.

Diphenyl Ether Derivatives 2,4-dichloro-4'-nitrodiphenyl ether, 2,4,6-trichlorophenyl ether, 2,4-dichloro-6-fluoro-4'-nitrodiphenyl ether 2-chloro-4-trifluoromethyl-3'-carboxy-4'-nitrodiphenyl ether and its salt and ester derivatives, 3-methyl-4'-nitrodiphenyl ether, 3,5-dimethyl-4'-nitrodiphenyl ether, 2,4'-dinitro-4-trifluoromethyldiphenyl ether, 2,4-dichloro-3'-methoxy-4'-nitrodiphenyl ether, sodium 5-(2-chloro-4-trifluoromethylphenoxy)-2-nitrobenzoate.

Anilides

N-(3,4-dichlorophenyl)propionamide, N-(3,4-dichlorophenyl)methacrylamide, N-(3-chloro-4-methylphenyl)-2-methylpentanamide, N-(3,4-dichlorophenyl)trimethylacetamide, N-(3,4-dichlorophenyl)-beta,beta-dimethylvaleramide, N-isopropyl-N-phenylchloroacetamide, N-n-butoxymethyl-N-(2,6-diethylphenyl)chloroacetamide and N-n-methoxy-methyl-N-(2,6-diethylphenyl)chloroacetamide, 2-chloro-N-(2-ethyl-6-methylphenyl)-N-(2-methoxy-1-methylethyl)-acetamide.

Uracils 5-bromo-3-s-butyl-6-methyluracil, 5-bromo-3-cyclohexyl-1,6-dimethyluracil, 3-cyclohexyl-5,6-trimethyleneuracil, 5-bromo-3-isopropyl-6-methyluracil and 3-tertbutyl-5-chloro-6-methyluracil.

Nitriles 2,6-dichlorobenzonitrile, diphenylacetonitrile, 3,5-dibromo-4-hydroxybenzonitrile, and 3,5-diiodo-4-hydroxybenzonitrile.

Other Organic Herbicides 2-chloro-N,N-diallylacetamide, N-(1,1-dimethyl-2-propynyl)-3,5-dichlorobenzamide, maleic hydrazide, 3-amino-1,2,4-triazole, monosodium methanearsonate, N,N-diallyl-2-chloroacetamide, disodium methanearsonate, N,N-dimethyl-beta,beta-diphenylacetamide, N,N-di(n-propyl)-2,6-dinitro-4-trifluoromethylaniline, N,N-di(n-propyl)-2,6-dinitro-4-methylaniline, N,N-di(n-propyl)-2,6-dinitro-4-methylsulfonylaniline, $N^3,N^3$-di-n-propyl-2,4-dinitro-6-trifluoromethyl-m-phenylenediamine, 3,5-dinitro-$N^4,N^4$-dipropylsulfanilamide, 4-isopropyl-2,6-dinitro-N,N-dipropylaniline, N-(2-chloroethyl)-2,6-dinitro-N-propyl-4-trifluoromethylaniline, O-(2,4-dichlorophenyl)-O-methylisopropylphosphoramidothioate, 4-amino-3,5,6-trichloropicolinic acid, 2,3-dichloro-1,4-naphthoquinone, di-(methoxythiocarbonyl)disulfide, 3-isopropyl-1H-2,1,3-benzothiadiazine(4)3H-one 2,2-dioxide, 6,7-dihydrodipyridol-[1,2-a:2',1'-c]pyrazidinium salts, 1,1'-dimethyl-4,4'-bipyridinium salts and 3,4,5,6-tetrahydro-3,5-dimethyl-2-thio-2H-1,3,5-thiadiazine, 2-(alpha-naphthoxy)-N-diethylacetamide, 2-N-(1-napthyl-aminocarbonyl)benzoic acid, 3-isopropyl-1H-2,1,3-benothiadiazin-4(3H)-one 2,2-dioxide, methyl-2-[4-(4-chlorophenoxy)phenoxy]-propionate, methyl-2-[4-(3,5-dichloro-pyrid-2-yl)phenoxy]propionate, 2-[1-(allyloxyamino)-propylidene]4-carbomethoxy-5,5-dimethylcyclohexane-1,3-dione.

When mixtures of herbicides are employed, the relative proportions which are used will depend upon the crop to be treated and the degree of selectivity in weed control desired.

EXAMPLE 1

3-(Cyclopentylmethylsulfonyl)-N,N-diethyl-1,2,4-triazole-1-carboxamide

Step A—Cyclopentylmethyl Methanesulfonate

Cyclopentanemethanol (50.0 g; 0.484 mol) and methane-sulfonyl chloride (67.0 g; 0.581 mol) in toluene (500 ml) were stirred and cooled to 4° C. Triethylamine (68.0 g; 0.678 mol) was added dropwise with external cooling so that the reaction temperature remained below 20° C. The reaction mixture is stirred under dry nitrogen at room temperature overnight. The reaction mixture was quenched with water (500 ml) and ether (500 ml), the organic phase separated, washed with water (500 ml) and saturated brine (500 ml) and dried (MgSO$_4$). The solution is filtered and the solvent evaporated, to afford cyclopentylmethyl methanesulfonate (86.0 g; 100% yield) as a colorless liquid. NMR - d(CDCl$_3$; 60 MHz) 0.8–2.6 (9H, m), 3.1 (3H, s) and 4.15 (2H, d, J=8 Hz).

Step B—Cyclopentylmethyl 1,2,4-Triazol-3-yl Sulfide 1,2,4-Triazole-3-thiol (49.0 g; 0.484 mol) and 86% potassium hydroxide (32.0 g; 0.484 mol) were dissolved in methanol (500 ml) and refluxed for 1 h. The solution was then evaporated to dryness, and the residue redissolved in methanol (500 ml). Cyclopentylmethyl methanesulfonate (86.0 g; 0.484 mol) was added, the solution stirred under reflux for 8 h, and at room temperature overnight. The solution was evaporated and the residue dissolved in ether (500 ml) and water (1 l). The aqueous layer was separated and extracted with another portion of ether (500 ml). The ether solutions were combined, washed with saturated brine (500 ml), dried (MgSO$_4$), filtered and evaporated, to afford cyclopentylmethyl 1,2,4-triazol-3-yl sulfide (85.0 g; 96%) as a waxy, white solid. NMR - d(CDCl$_3$; 60 MHz) 1.0–2.4 (10H, m), 3.2 (2H, d, J=7 Hz), 8.1 (1H, s) and 13.4 (1H, br s).

Step C—Cyclopentylmethyl 1,2,4-Triazol-3-yl Sulfone

Cyclopentylmethyl 1,2,4-triazol-3-yl sulfide (8.9 g; 49 mmol) was stirred in glacial acetic acid (50 ml), 50% hydrogen peroxide (7 ml; 120 mmol) added, and the mixture stirred at 95°–99° C. for 1.5 h. The volume of the solution was reduced to approximately 20 ml by evaporation and a solid separated, which was filtered off, washed with 30% acetic acid and dried to afford cyclopentylmethyl 1,2,4-triazol-3-yl sulfone (3.8 g; 36%) as white flakes, m.p. 150°–155° C. NMR - d(CD$_3$SOCD$_3$) 1.0–2.4 (9H, m), 3.6 (2H, d, J=7 Hz) and 9.0 (1H, s). IR - vmax (nujol) 3160, 1325, 1245, 1140, 1005, 980 and 885 cm$^{-1}$.

Step D—3-(Cyclopentylmethylsulfonyl)-N,N-diethyl-1,2,4-triazole-1-carboxamide Diethylcarbamoyl chloride (0.65 ml; 5.08 mmol) was added to cyclopentylmethyl 1,2,4-triazol-3-yl sulfone (1.00 g; 4.65 mmol) in dry pyridine (5 ml) under dry nitrogen, and the solution stirred at room temperature overnight. The resulting mixture was poured into 2M hydrochloric acid (20 ml) at 3° C. and the mixture extracted into ethyl acetate (3×30 ml). The extracts were combined, dried (Na$_2$SO$_4$), filtered and evaporated, to afford 3-(cyclopentylmethylsulfonyl)-N,N-diethyl-1,2,4-triazole-1-carboxamide (1.44 g; 99%) as white crystals, m.p. 77°–79° C., (Found, C: 49.82; H: 6.75; N: 17.96; S: 10.44. C$_{13}$H$_{22}$N$_4$O$_3$S requires C: 49.66; H: 7.05; N: 17.82; S: 10.20%) NMR - d(CDCl$_3$; 60 MHz) 1.0–2.6 (15H, m), 3.3–3.8 (6H, m) and 9.0 (1H, s).

EXAMPLE 2

3-(Cyclohexylmethylsulfonyl)-N,N-diethyl-1,2,4-triazole-1-carboxamide

Step A—Cyclohexylmethyl 1,2,4-Triazol-3-yl Sulfide

Cyclohexylmethyl bromide (42 ml; 0.30 mol) was added over 5 min to 1,2,4-triazole-3-thiol (30.3 g; 0.30 mol) and sodium methoxide (17.3 g; 0.32 mol) in dry methanol (250 ml) under dry nitrogen. The mixture was refluxed for 4 h, stirred at room temperature overnight and evaporated. The residue was dissolved in ethyl acetate (400 ml) and water (200 ml). The organic phase is separated, washed with water (100 ml), dried (Na$_2$SO$_4$), filtered and its volume reduced by evaporation, causing a solid to precipitate. The solid was filtered off and dried, to afford cyclohexylmethyl 1,2,4-triazol-3-yl sulfide (48.0 g; 81%) as white plates, m.p. 74°–78° C. (Found, C: 54.98; H: 7.85; N: 21.32; S: 16.13. C$_9$H$_{15}$N$_3$S requires C: 54.79; H: 7.66; N: 21.30; S: 16.25%). NMR - d(CDCl$_3$; 90 MHz) 0.50–2.10 (11H, m), 3.1 (2H, d, J=6.4 Hz), 8.13 (1H, s) and 13.9 (1H, br s).

Step B—Cyclohexylmethyl 1,2,4-Triazol-3-yl Sulfone

Cyclohexylmethyl 1,2,4-triazol-3-yl sulfide (39.6 g; 0.20 mol) was dissolved in glacial acetic acid (200 ml), 50% hydrogen peroxide (28 ml; 0.49 mol) added, and the solution stirred at 95°–105° C. for 2 h. After standing at room temperature a solid precipitated, which was filtered off and dried, to afford cyclohexylmethyl 1,2,4-triazol-3-yl sulfone (41.8 g; 90%) as white flakes, m.p. 172°–175° C., (Found, C: 47.04; H: 6.51; N: 18.19; S:

13.90. $C_9H_{15}N_3O_2S$ requires C: 47.14; H: 6.59; N: 18.33; S: 13.98%). NMR - d($CD_3SOCD_3$; 90 MHz) 0.8–2.1 (11H, m), 3.35. (2H, d, J=5.9 Hz), 8.90 (1H, s) and 15.1 (1H, br s).

Step C—3-(Cyclohexylmethylsulfonyl)-N,N-diethyl-1,2,4-triazole-1-carboxamide

Diethylcarbamoyl chloride (1.2 ml; 9.4 mmol) was added to cyclohexylmethyl 1,2,4-triazol-3-yl sulfone (2.0 g; 8.7 mmol) in dry pyridine (10 ml) under dry nitrogen, and the solution stirred at room temperature overnight. The resulting mixture was poured into 2M hydrochloric acid (40 ml) at 2° C. and the cloudy solution extracted into ethyl acetate (3×60 ml). The extracts were combined, dried ($Na_2SO_4$), filtered and evaporated, to afford a colorless oil which was dissolved in 95% dichloromethane, 5% acetonitrile, and the solution filtered through silica. Evaporation afforded 3-(cyclohexylmethylsulfonyl)-N,N-diethyl-1,2,4-triazole-1-carboxamide (2.82 g; 98%) as white crystals, m.p. 40°–46° C. (Found, C: 51.04; H: 7.39; N: 17.01; S: 9.81. $C_{14}H_{24}N_4O_3S$ requires C: 51.20; H: 7.37; N: 17.06; S: 9.76%). NMR - d($CDCl_3$; 90 MHz) 0.80–2.30 (17H, m), 3.31 (2H, d, J=6.1 Hz), 3.61 (4H, m) and 8.92 (1H, s).

EXAMPLE 3

3-(Cyclohexylmethylsulfonyl)-N,N-diallyl-1,2,4-triazole-1-carboxamide

Diallylcarbamoyl chloride (1.3 ml; 9.6 mmol) was added to cyclohexylmethyl 1,2,4-triazol-3-yl sulfone (2.0 g; 8.7 mmol) in dry pyridine (10 ml) under dry nitrogen, and the solution stirred at room temperature overnight. The resulting mixture was poured into 2M hydrochloric acid (50 ml) at 3° C. and the solution extracted into ethyl acetate (3×60 ml). The extracts were combined, dried ($Na_2SO_4$), filtered and evaporated, affording 3-(cyclohexylmethylsulfonyl)-N,N-diallyltriazole-1-carboxamide (2.85 g; 92%) as a pale yellow, viscous liquid, (Found, C: 54.44; H: 6.62; N: 15.79; S: 8.88. $C_{16}H_{25}N_4O_3S$ requires C: 54.39; H: 7.08; N: 15.86; S:9.07%). NMR - d($CDCl_3$; 60 MHz) 0.7–2.3 (11H, m), 3.3 (2H, d, J=5 Hz), 4.2 (4H, d, J=6 Hz), 5.0–5.4 (4H, m), 5.6–6.3 (2H, m) and 9.0 (1H, s).

EXAMPLE 4

Cycloheptylmethylsufonyl)-N,N-diethyl-1,2,4-triazole-1-carboxamide

Step A—Cycloheptylmethyl 1,2,4-Triazol-3-yl Sulfide

Cycloheptylmethyl bromide (3.5 g; 18 mmol) was added in one portion to 1,2,4-triazole-3-thiol (1.86 g; 18.4 mmol) and sodium methoxide (1.09 g; 20 mmol) in dry methanol (20 ml) under dry nitrogen. The solution was stirred at room temperature overnight, refluxed for 2 h and the solvent evaporated. The residue was dissolved in ethyl acetate (30 ml) and water (15 ml), the organic phase separated, washed with water (15 ml) and saturated brine (5 ml), dried ($Na_2SO_4$), filtered and evaporated to afford a pale yellow liquid (3.8 g). Flash chromatography (75% dichloromethane, 25% acetonitrile) afforded cycloheptylmethyl 1,2,4-triazol-3-yl sulfide (1.69 g; 44% yield) as a sticky white solid. NMR - d($CDCl_3$; 60 MHz) 0.7–2.1 (13H, m), 3.1 (2H, d, J=6 Hz) and 8.3 (1H,s).

Step B—Cycloheptylmethyl 1,2,4-Triazol-3-yl Sulfone

Cycloheptylmethyl 1,2,4-triazol-3-yl sulfide (1.69 g; 8.0 mmol) was stirred in glacial acetic acid (7 ml), 50% hydrogen peroxide (1.2 ml; 20 mmol) added, and the mixture stirred at 95°–120° C. for 1.5 h. The solution was evaporated to dryness, to afford cycloheptylmethyl 1,2,4-triazol-3-yl sulfone (1.87 g; 96% yield) as a white solid.

Step C—3-(Cycloheptylmethylsufonyl)-N,N-diethyl-1,2,4-triazole-1-carboxamide

Diethylcarbamoyl chloride (1.15 ml; 9.0 mmol) was added to cycloheptylmethyl 1,2,4-triazol-3-yl sulfone (1.87 g; 7.7 mmol) in dry pyridine (10 ml) under dry nitrogen, and the solution stirred at room temperature overnight. The resulting mixture was poured into 2M hydrochloric acid (40 ml) at 4° C. and the mixture extracted into ethyl acetate (3×60 ml). The extracts were combined, dried ($Na_2SO_4$), filtered and evaporated to afford a colorless oil (2.9 g); flash chromatography (90% dichloromethane, 10% acetonitrile) afforded 3-(cycloheptylmethylsulfonyl)-N,N-diethyl-1,2,4-triazole-1-carboxamide (2.47 g; 94%) as white crystals, m.p. 46°–51° C., (Found, C: 52.61; H: 7.45; N: 16.45; S: 9.37. $C_{15}H_{26}N_4O_3S$ requires C: 52.61; H: 7.65; N: 16.36; S: 9.36%). NMR - d($CDCl_3$; 60 MHz) 0.9–2.6 (19H, m), 3.2–3.8 (6H, m) and 8.9 (1H, s).

EXAMPLE 5

3-(Cyclopentylmethylsulfonyl)-N,N-dimethyl-1,2,4-triazole-1-carbothioamide

Dimethylthiocarbamoyl chloride (3.1 g; 25 mmol) was added to cyclopentylmethyl 1,2,4-triazol-3-yl sulfone (5.0 g; 23 mmol) in pyridine (20 ml), and the solution stirred at 35° C. for 2 h and at room temperature overnight. The resulting mixture was evaporated and the residue dissolved in 10% hydrochloric acid (100 ml) and ether (100 ml). The organic solution was separated, washed with brine, dried ($MgSO_4$) and evaporated, to afford the product as a semi-solid. Recrystallisation from ether afforded 3-(cyclopentylmethylsulfonyl)-N,N-dimethyl-1,2,4-triazole-1-carbothioamide (6.0 g; 86%), m.p. 65° C., (Found, C: 43.53; H: 5.93; N: 18.51; S: 21.19. $C_{11}H_{18}N_4O_2S_2$ requires C: 43.69; H: 6.00; N: 18.53; S: 21.20%). NMR - d($CDCl_3$; 60 MHz) 1.0–2.7 (m), 2.9–3.7 (8H, m) and 9.0 (1H, s).

EXAMPLE 6

3-(Cyclopentylmethylsulfonyl)-N,N-diethyl-1,2,4-triazole-1-carbothioamide

Diethylthiocarbamoyl chloride (3.8 g; 25 mmol) was added to cyclopentylmethyl 1,2,4-triazol-3-yl sulfone (5.0 g; 23 mmol) in pyridine (20 ml), and the solution stirred at 36° C. for 2 h and at room temperature overnight. The resulting mixture was evaporated and the residue dissolved in 10% hydrochloric acid (100 ml) and ether (100 ml). The organic solution was separated, washed with brine, dried ($MgSO_4$) and evaporated, to afford the product as a semi-solid. Recrystallisation from ether afforded 3-(cyclopentylmethylsulfonyl)-N,N-diethyl-1,2,4-triazole-1-carbothioamide (7.0 g; 92%), m.p. 78° C., (Found, C: 46.94; H: 6.60; N: 16.92; S: 19.23. $C_{13}H_{22}N_4O_2S_2$ requires C: 47.25; H: 6.91; N: 16.95; S: 19.40%) NMR - d($CDCl_3$; 60 MHz) 0.8–2.6 (15H, m), 3.3–4.2 (6H, m) and 9.0 (1H, s).

EXAMPLE 7

(Cyclopropylmethylsulfonyl)-N,N-diethyl-1,2,4-triazole-1-carboxamide

Step A—Cyclopropylmethyl Methanesulfonate

Cyclopropylcarbinol (27.4 g; 0.373 mol) and methanesulfonyl chloride (47.56 g; 0.407 mol) in dry ether (250 ml) was cooled to $-20°$ C. under dry nitrogen. Triethylamine (59 ml; 0.42 mol) is added dropwise over 45 min with external cooling so that the reaction temperature remained below $-15°$ C. The reaction mixture was allowed to warm to room temperature over 2 h and then filtered. The solid material is washed with ether. The solutions were combined and evaporated, to afford crude cyclopropylmethyl methanesulfonate (58.36 g) as a pale yellow liquid, which was used without further purification. NMR - $d(CDCl_3;$ 60 MHz) 0.3–1.5 (5H, m), 3.0 (3H, s) and 4.0 (2H, d, J=7 Hz).

Step B—Cyclopropylmethyl 1,2,4-Triazole-3-yl Sulfide 1,2,4-Triazole-3-thiol (20.2 g; 0.20 mol) and sodium methoxide (11.8 g; 0.22 mol) were dissolved in methanol (250 ml) and cyclopropylmethyl methanesulfonate (32.3 g; 0.215 mol) added. The mixture was refluxed for 25 min under dry nitrogen, allowed to cool to 40° C. and filtered. The solid was washed with ethyl acetate and the organic solutions combined and evaporated. The residue was dissolved in water (250 ml) and the solution extracted with ethyl acetate ($2 \times 250$ ml). The extracts were combined, washed with saturated brine (200 ml), dried ($Na_2SO_4$), filtered and evaporated, giving cyclopropylmethyl 1,2,4-triazol-3-yl sulfide (19.7 g; 64%) as a pale yellow pasty solid. NMR - $d(CDCl_3+CD_3SOCD_3;$ 90 MHz) 0.1–0.7 (4H, m), 0.9–1.4 (1H, m), 3.1 (2H, d, J=7 Hz), 8.1 (1H, s).

Step C—Cyclopropylmethyl 1,2,4-Triazol-3-yl Sulfone

Cyclopropylmethyl 1,2,4-triazol-3-yl sulfide (18.57 g; 0.12 mol) was stirred in glacial acetic acid (100 ml) and 50% hydrogen peroxide (20 g; 0.29 mol) at room temperature for 16 h and at 105° C. for 2 h. Evaporation afforded a residue which was crystallised from ethanol and ethyl acetate to afford cyclopropylmethyl 1,2,4-triazol-3-yl sulfone (10.3 g; 46%) as white crystals, m.p. 140°–149° C., (Found, C: 38.56; H: 4.76; N: 22.57; S: 17.29. $C_6H_9N_3O_2S$ requires C: 38.49; H: 4.85; N: 22.44; S: 17.11%). NMR - $d(CD_3SOCD_3;$ 60 MHz) 0.1–0.8 (4H, m), 0.8–1.3 (1H, m), 3.2 (2H, d, J=7 Hz), 8.8 (1H, s) and 9.5 (1H, s).

Step D—3-(Cyclopropylmethylsulfonyl)-N,N-diethyl-1,2,4-triazole-1-carboxamide Diethylcarbamoyl chloride (1.55 ml; 11.8 mmol) was added to cyclopropylmethyl 1,2,4-triazol-3-yl sulfone (2.07 g; 11.1 mmol) in dry pyridine (10 ml) under dry nitrogen. The resulting solution was stirred at room temperature overnight. The resulting mixture was poured into cold 2M hydrochloric acid (40 ml) and the cloudy solution extracted into ethyl acetate ($3 \times 50$ ml). The extracts were combined, washed with saturated brine (50 ml), dried ($Na_2SO_4$), filtered and evaporated to afford 3-(cyclopropylmethylsulfonyl)-N,N-diethyl-1,2,4-triazole-1-carboxamide (3.10 g; 98%) as white crystals, m.p. 68°–74° C., (Found, C: 46.23; H: 6.24; N: 19.60; S: 11.29. $C_{11}H_{18}N_4O_3S$ requires C: 46.14; H: 6.34; N: 19.57; S: 11.20%) NMR - $d(CDCl3;$ 60 MHz) 0.2–0.9 (4H, m), 0.9–1.5 (7H, m), 3.3 (2H, d, J=7 Hz), 3.6 (4H, q, J=7 Hz) and 8.9 (1H, s). IR vmax ($CHCl_3$) 3040, 1710, 1440, 1340, 1270, 1180, 1150, 1030, 870 and 635 $cm^{-1}$.

EXAMPLE 8

3-(Cyclobutylmethylsulfonyl)-N,N-diethyl-1,2,4-triazole-1-carboxamide

Step A—Cyclobutylmethyl Methanesulfonate

Cyclobutanemethanol (24.9 g; 0.287 mol) and methanesulfonyl chloride (35.3 g; 0.302 mol) in dry ether (250 ml) was cooled to $-20°$ C. under dry nitrogen. Triethylamine (44 ml; 0.32 mol) was added dropwise over 15 min with external cooling so that the reaction temperature remained below $-5°$ C. The reaction mixture was allowed to warm to room temperature over 1 h and then filtered. The remaining solid was washed with ether. The ether solutions were combined and the ether evaporated, to afford crude cyclobutylmethyl methanesulfonate (48.75 g) as a pale yellow liquid, which was used in the next step without further purification. NMR - $d(CDCl_3;$ 60 MHz) 1.6–2.9 (7H, m), 3.0 (3H, s) and 4.1 (2H, d, J=7 Hz).

Step B—Cyclobutylmethyl 1,2,4-Triazol-3-yl Sulfide

To a solution of 1,2,4-triazole-3-thiol (20.2 g; 0.20 mol) and sodium methoxide (11.8 g; 0.22 mol) in methanol (250 ml) is added cyclobutylmethyl methanesulfonate (36.4 g; 0.22 mol). The mixture was refluxed for 27 h under dry nitrogen, allowed to cool to 25° C. and filtered. The solid was washed with ethyl acetate and the organic solutions combined and evaporated. The residue was dissolved in water (250 ml) and extracted into ethyl acetate (250 ml) and dichloromethane (100 ml). The extracts were combined, dried ($Na_2SO_4$), filtered and evaporated to afford crude cyclobutylmethyl 1,2,4-triazol-3-yl sulfide (21.8 g; 65%) as a white, sticky solid. NMR -$d(CDCl_3;$ 60 MHz) 1.5–2.8 (m), 3.2 (2H, d, J=7 Hz), 8.0 (1H, s) and 12.4 (1H, br s).

Step C—Cyclobutylmethyl 1,2,4-Triazol-3-yl Sulfone

Cyclobutylmethyl 1,2,4-triazol-3-yl sulfide (20.8 g; 0.123 mol) was refluxed in glacial acetic acid (120 ml) and 50% hydrogen peroxide (22 g; 0.32 mol) for 2 h. Evaporation afforded a residue which was crystallised from ethanol and ethyl acetate to afford cyclobutylmethyl 1,2,4-triazol-3-yl sulfone (15.7 g; 64%) as white crystals, m.p. 125°–34° C. NMR - $d(CD_3SOCD_3;$ 60 MHz) 1.5–2.2 (6H, m), 2.3–3.0 (1H, m), 3.5 (2H, d, J=7 Hz), 8.8 (1H, s) and 12.8 (1H, s).

Step D—(Cyclobutylmethylsulfonyl)-N,N-diethyl-1,2,4-triazole-1-carboxamide

Diethylcarbamoyl chloride (1.49 ml; 11.3 mmol) was added to cyclobutylmethyl 1,2,4-triazol-3-yl sulfone (2.06 g; 10.2 mmol) in dry pyridine (10 ml) under dry nitrogen, and the solution stirred at room temperature overnight. The reaction mixture was poured into cold 2M hydrochloric acid (60 ml) and the cloudy solution extracted with two portions of ethyl acetate (120 ml and 50 ml). The extracts were combined, washed with saturated brine (50 ml), dried ($Na_2SO_4$), filtered and the volume of solution reduced by evaporation until a white solid precipitates. Hexane was added to the mixture which was then cooled and the solid filtered off to afford 3-(cyclobutylmethylsulfonyl)-N,N-diethyl-1,2,4- triazole-1-carboxamide (2.40 g; 78%) as white crystals, m.p. 113°-116° C., (Found, C: 47.96; H: 6.56; N: 18.51; S: 10.85. $C_{12}H_{20}N_4O_3S$ requires C: 47.98; H: 6.71; N: 18.65; S: 10.67%). NMR - d($CDCl_3$; 60 MHz) 1.3 (6H, t, J=7 Hz), 1.5-2.4 (6H, m), 2.4-3.2 (1H, m), 3.4-3.8 (6H, m) and 8.9 (1H, s). IR vmax ($CHCl_3$) 3000, 1710, 1440, 1340, 1270, 1180, 1145, 1030 and 870 $cm^{-1}$.

Alternate Preparation

Cyclopentylmethyl 1,2,4-Triazol-3-yl Sulfide

Cyclopentylmethyl bromide (21 g; 0.13 mol) was added in one portion to 1,2,4-triazole-3-thiol (12.3 g; 0.12 mol) and sodium methoxide (7.1 g; 0.13 mol) in dry methanol (100 ml) under dry nitrogen. The mixture was stirred at room temperature for 3 days, refluxed for 3 h and evaporated. The residue was dissolved in ethyl acetate (200 ml) and water (100 ml), the organic phase separated, washed with water (100 ml), dried ($Na_2SO_4$), filtered and evaporated, to afford cyclopentylmethyl 1,2,4-triazol-3-yl sulfide (18.1 g; 82%) as a waxy, off-shite solid, m.p. 48°-55° C.

One skilled in the art will appreciate that the above examples are merely illustrative and are capable of a wide variation and modification without departing from the sprit of this invention as defined by the claims.

TEST PROCEDURE

This example shows the selective herbicide activity of the triazolecarboxamides of the invention exhibited on the following representative species:

|  |  |  | Approximate No. Seeds |
|---|---|---|---|
| Monocots: | Barnyardgrass | (Echinochloa crusgalli) | 25 |
|  | Foxtail | (Setaria spp) | 25 |
|  | Johnsongrass | (Sorghum halepense) | 25 |
|  | Nutsedge | (Cyperus esculentus) | 5 |
|  | Wild Oats | (Avena fatua) | 20 |
| Dicots: | Cocklebur | (Xanthium pensylvanicum) | 3 |
|  | Morningglory | (Ipomoea spp) | 10 |
|  | Velvetleaf | (Abutilon theophrasti) | 15 |
|  | Sicklepod | (Cassia obtusifolia) | 5 |
|  | Pigweed | (Amaranthus retroflexus) | 15 |
| Crops: | Corn | (Zea mays) | 5 |
|  | Cotton | (Gossypium hirsutum) | 5 |
|  | Rice | (Oryza sativa) | 10 |
|  | Soybeans | (Glycine max) | 5 |
|  | Sugarbeets | (Beta vulgaris) | 10 |
|  | Wheat | (Triticum spp.) | 10 |

The following test procedure is employed. Seeds of the above species are planted in soil in trays (approx. 7"×10½×3"). For preemergence tests, the trays are sprayed with the test compound immediately after planting. For postemergence tests, the seeds are allowed to germinate and after growing in the greenhouse for two weeks, the growing plants are treated with the test compound. The compound to be evaluated is dissolved in acetone or water and sprayed over the trays using a carrier volume equivalent to 50 gallons per acre at the rate of application (in pounds per acre, lb/A) specified in the table. About two weeks after application of the test compound, the state of growth of the plants is observed and the phytotoxic effect of each compound determined as follows: each species is evaluated on a scale of 0-100 in which 0=no activity and 100=total kill and the results for the monocots and dicots separately averaged. The following table shows the results obtained for the compounds of the invention.

PRIMARY HERBICIDE DATA

| Ex. No. | APP | LB AI | AM | AD | BYG | FOX | JON | NUT | WO | CKL | MG | PIG | SIC | VEL |
|---|---|---|---|---|---|---|---|---|---|---|---|---|---|---|
| 1 | R | 20 | 80 | 05 | 100 | 100 | 100 | 00 | 99 | — | 00 | — | 00 | 15 |
| 1 | S | 20 | 31 | 23 | 60 | 45 | 21 | 00 | 31 | 05 | 85 | — | — | 00 |
| 2 | R | 05 | 77 | 07 | 100 | 100 | 75 | 40 | 70 | 00 | 10 | — | 10 | — |
| 2 | R | 20 | 100 | 35 | 100 | 100 | 100 | 100 | 100 | 00 | 15 | — | 90 | — |
| 2 | S | 05 | 06 | 08 | 10 | 05 | 10 | 00 | 05 | 10 | 15 | — | 00 | — |
| 2 | S | 20 | 11 | 15 | 10 | 10 | 15 | 00 | 20 | 15 | 20 | — | 10 | — |
| 3 | R | 20 | 72 | 00 | 99 | 100 | 80 | 00 | 80 | 00 | 00 | — | 00 | 00 |
| 3 | S | 20 | 02 | 00 | 10 | 00 | 00 | 00 | 00 | 00 | 00 | — | — | 00 |
| 4 | R | 20 | 65 | 00 | 100 | 86 | 96 | 00 | 41 | 00 | 00 | — | 00 | 00 |
| 4 | S | 20 | 01 | 08 | 00 | 05 | 00 | 00 | 00 | 00 | 10 | — | — | 15 |
| 5 | R | 20 | 67 | 00 | 60 | 90 | 90 | 71 | 25 | 00 | 00 | 00 | 00 | 00 |
| 5 | S | 20 | 02 | 00 | 00 | 00 | 10 | 00 | 00 | 00 | 00 | 00 | 00 | 00 |
| 6 | R | 20 | 52 | 00 | 70 | 100 | 90 | 00 | 00 | — | 00 | 00 | 00 | 00 |
| 6 | S | 20 | 08 | 00 | 00 | 00 | 41 | 00 | 00 | 00 | 00 | 00 | 00 | 00 |
| 7 | R | 05 | 79 | 44 | 61 | 100 | 71 | 100 | 61 | 00 | 51 | 100 | — | 40 |
| 7 | R | 20 | 90 | 74 | 90 | 100 | 81 | 100 | 81 | 00 | 70 | 100 | — | 100 |
| 7 | S | 05 | 00 | 06 | 00 | 00 | 00 | 10 | 00 | 00 | 10 | 06 | — | 16 |
| 7 | S | 20 | 31 | 29 | 51 | 10 | 81 | 00 | 11 | 00 | 98 | 10 | — | 15 |
| 8 | R | 05 | 71 | 41 | 75 | 90 | 71 | 90 | 31 | 00 | 41 | 100 | — | 15 |
| 8 | R | 20 | 85 | 66 | 70 | 95 | 91 | 100 | 71 | 00 | 41 | 100 | — | 100 |
| 8 | S | 05 | 27 | 03 | 41 | 00 | 81 | 00 | 11 | 05 | 10 | 00 | — | 00 |

PRIMARY HERBICIDE DATA -continued

| Ex. No. | APP | LB AI | AM | AD | BYG | FOX | JON | NUT | WO | CKL | MG | PIG | SIC | VEL |
|---|---|---|---|---|---|---|---|---|---|---|---|---|---|---|
| 8 | S | 20 | 39 | 18 | 71 | 41 | 71 | 00 | 11 | 20 | 15 | 15 | — | 25 |

APP: R = Pre-emergence; S = Post-emergence
LB/AI = lbs. per acre of active ingredient. values given as tenths of lbs.
BYG = Barnyardgrass
FOX = Foxtail
JON = Johnsongrass
NUT = Yellow nutsedge
WO = Wild oat
CKL = Cocklebur
MG = Morningglory
PIG = Pigweed
SIC = Sicklepod
VEL = Velvetleaf
WHT = Wheat
CN = Corn
COT = Cotton
RI = Rice
SB = Sugarbeets
SOY = Soybeans The following is a pre-emergence "secondary" herbicide test which is more extensive than the primary in both species tested and rates of application.
The same procedure is followed as in the primary herbicide test.

SECONDARY HERBICIDE TEST

| Ex. | RATE | AD | AM | AND | BID | BND | CKL | MG | NS | PIG | SIC | TEA | VEL | BYG | CAN |
|---|---|---|---|---|---|---|---|---|---|---|---|---|---|---|---|
| 1 | 2.0 | 79 | 100 | 100 | 100 | 100 | 0 | 0 | 100 | 100 | 95 | 100 | 100 | 100 | 100 |
| 1 | 1.0 | 65 | 86 | 65 | 100 | 100 | 0 | 0 | 100 | 100 | 80 | 11 | 100 | 100 | 100 |
| 1 | 0.5 | 25 | 83 | 0 | 25 | 0 | 0 | 0 | 100 | 100 | 15 | 11 | 0 | 100 | 100 |
| 5 | 2.0 | 20 | 50 | 0 | 10 | 0 | 0 | 0 | 98 | 100 | 0 | 0 | 0 | 98 | 90 |
| 5 | 1.0 | 17 | 46 | 0 | 10 | 0 | 0 | 0 | 95 | 65 | 0 | 0 | 0 | 95 | 80 |
| 5 | 0.5 | 3 | 10 | 0 | 0 | 0 | 0 | 0 | 11 | 21 | 0 | 0 | 0 | 0 | 60 |
| 6 | 2.0 | 29 | 64 | 0 | 95 | 0 | 0 | 0 | 100 | 95 | 0 | 0 | 0 | 100 | 100 |
| 6 | 1.0 | 16 | 44 | 0 | 0 | 0 | 0 | 0 | 95 | 65 | 0 | 0 | 0 | 100 | 50 |
| 6 | 0.5 | 11 | 35 | 0 | 0 | 0 | 0 | 0 | 100 | 11 | 0 | 0 | 0 | 95 | 11 |

| Ex. | RATE | FOX | JON | NUT | SIG | SMB | WO | CN | COT | RI | SB | SOY | WHT | AD | WM |
|---|---|---|---|---|---|---|---|---|---|---|---|---|---|---|---|
| 1 | 2.0 | 100 | 100 | 100 | 100 | 100 | 100 | 95 | 0 | 25 | 81 | 51 | 98 | 95 | 95 |
| 1 | 1.0 | 100 | 100 | 15 | 100 | 80 | 100 | 81 | 0 | 40 | 51 | 31 | 95 | 85 | 85 |
| 1 | 0.5 | 100 | 100 | 5 | 100 | 65 | 98 | 60 | 0 | 0 | 10 | 0 | 71 | 41 | 41 |
| 5 | 2.0 | 98 | 10 | 0 | 98 | 0 | 11 | 0 | 0 | 0 | 0 | 0 | 0 | 0 | 0 |
| 5 | 1.0 | 95 | 0 | 0 | 95 | 0 | 10 | 0 | 0 | 0 | 0 | 0 | 0 | 0 | 0 |
| 5 | 0.5 | 11 | 0 | 0 | 10 | 0 | 0 | 0 | 0 | 0 | 0 | 0 | 0 | 0 | 0 |
| 6 | 2.0 | 100 | 95 | 0 | 99 | 0 | 21 | 0 | 0 | 0 | 0 | 0 | 0 | 0 | 0 |
| 6 | 1.0 | 95 | 15 | 0 | 98 | 0 | 0 | 0 | 0 | 0 | 0 | 0 | 0 | 0 | 0 |
| 6 | 0.5 | 100 | 5 | 0 | 75 | 0 | 0 | 0 | 0 | 0 | 0 | 0 | 0 | 0 | 0 |

SECONDARY HERBICIDE TEST

| Ex. | RATE | AD | AM | AND | BND | CKL | MG | NS | PIG | SIC | TEA | VEL | WM | BYG |
|---|---|---|---|---|---|---|---|---|---|---|---|---|---|---|
| 1 | 1.0 | 63 | 94 | 100 | 40 | 11 | 11 | 100 | 100 | 70 | 35 | 100 | 70 | 100 |
| 1 | 0.25 | 27 | 81 | 15 | 0 | 0 | 0 | 100 | 100 | 0 | 15 | 1 | 40 | 100 |
| 1 | 0.06 | 0 | 43 | 0 | 0 | 0 | 0 | 0 | 0 | 0 | 0 | 0 | 0 | 98 |
| 7 | 1.0 | 77 | 100 | 100 | 100 | 0 | 21 | 100 | 100 | 100 | 100 | 75 | 78 | 100 |
| 7 | 0.25 | 44 | 85 | 60 | 0 | 0 | 11 | 100 | 100 | 65 | 5 | 1 | 98 | 100 |
| 7 | 0.06 | 17 | 47 | 50 | 0 | 0 | 0 | 0 | 100 | 20 | 0 | 0 | 0 | 99 |
| 8 | 1.0 | 80 | 100 | 95 | 100 | 20 | 11 | 100 | 100 | 100 | 100 | 100 | 75 | 100 |
| 8 | 0.25 | 43 | 100 | 100 | 0 | 0 | 0 | 100 | 100 | 75 | 20 | 1 | 35 | 100 |
| 8 | 0.06 | 14 | 55 | 38 | 0 | 0 | 0 | 0 | 100 | 10 | 0 | 0 | 0 | 100 |

| Ex. | RATE | CAN | DB | FOX | JON | NUT | SIG | WO | CN | COT | RI | SB | SOY | WHT |
|---|---|---|---|---|---|---|---|---|---|---|---|---|---|---|
| 1 | 1.0 | 100 | 100 | 98 | 100 | 55 | 99 | 100 | 98 | 21 | 31 | 100 | 61 | 45 |
| 1 | 0.25 | 100 | 90 | 98 | 78 | 10 | 98 | 75 | 10 | 0 | 0 | 0 | 0 | 0 |
| 1 | 0.06 | 31 | 0 | 99 | 10 | 5 | 84 | 21 | 0 | 0 | 0 | 0 | 0 | 0 |
| 7 | 1.0 | 100 | 100 | 100 | 100 | 100 | 100 | 100 | 98 | 35 | 81 | 90 | 86 | 80 |
| 7 | 0.25 | 95 | 65 | 98 | 90 | 75 | 99 | 65 | 20 | 0 | 61 | 0 | 0 | 45 |
| 7 | 0.06 | 40 | 0 | 98 | 50 | 10 | 82 | 0 | 0 | 11 | 0 | 0 | 0 | 5 |
| 8 | 1.0 | 100 | 100 | 100 | 100 | 100 | 100 | 100 | 99 | 31 | 91 | 88 | 86 | 81 |
| 8 | 0.25 | 100 | 100 | 100 | 100 | 100 | 100 | 100 | 66 | 5 | 21 | 0 | 10 | 61 |
| 8 | 0.06 | 65 | 0 | 98 | 35 | 5 | 95 | 45 | 0 | 11 | 0 | 15 | 31 |

| Key to Secondary Herbicide Test | | |
|---|---|---|
| Rate: | lbs. per acre of active ingredient | |
| AND | Anoda | (*Anoda cristata*) |
| BID | Bidens | (*Bidens pilosa*) |
| BND | Bindweed | (*Convolvulus arvensis*) |
| CKL | Cocklebur | (*Xanthium pensylvanicum*) |
| MG | Morningglory | (*Ipomoea purpurea*) |
| NS | Nightshade | (*Solanum spp.*) |
| PIG | Pigweed | (*Amaranthus retroflexus*) |
| SIC | Sicklepod | (*Cassia obtusifolia*) |
| TEA | Teaweed | (*Sida spinosa*) |
| VEL | Velvetleaf | (*Abutilon theapharasti*) |
| WM | Wild mustard | (*Brassica kaber*) |
| BYG | Barnyardgrass | (*Echinochloa crus-galli*) |
| CAN | Canarygrass | (*Phalaris minor*) |
| DB | Downybrome | (*Bromus techorum*) |
| FOX | Foxtail | (*Setaria viridis*) |
| JON | Johnsongrass | (*Sorghum halepense*) |
| NUT | Nutsedge | (*Cyperus esculentus*) |
| SIG | Signalgrass | (*Brachiaria platyphylla*) |
| SMB | Smoothbrome | (*Bromus inermis*) |
| WO | Wild oat | (*Avena fatua*) |
| CN | Corn | (*Zea mays*) |
| COT | Cotton | (*Gossypium hirsutum*) |
| RI | Rice | (*Oryza sativa*) |
| SB | Sugarbeets | (*Beta vulgaris*) |
| SOY | Soybeans | (*Glycine max*) |
| WHT | Wheat | (*Triticum spp.*) |

By following substantially the procedure described in the examples above and by substituting the appropriate starting material the following products may be prepared.

$$\begin{array}{c} X \\ \| \\ RR^1NC-N \end{array} \diagup \begin{array}{c} CH=N \\ | \\ N=CSO_2CH_2R^2 \end{array}$$

| Ex. No. | R | R$^1$ | R$^2$ | X |
|---|---|---|---|---|
| 9 | CH$_3$ | CH$_3$ | cyclopentyl | O |
| 10 | C$_3$H$_7$— | C$_3$H$_7$— | cyclopentyl | O |
| 11 | C$_4$H$_9$— | C$_4$H$_9$— | cyclopentyl | S |
| 12 | C$_5$H$_{11}$— | C$_5$H$_{11}$— | cyclopentyl | O |
| 13 | C$_6$H$_{13}$— | C$_6$H$_{13}$— | cyclopentyl | O |
| 14 | CH$_2$=CH— | CH$_2$=CH— | cyclopentyl | O |
| 15 | CH$_2$=CHC$_2$H$_4$— | CH$_2$=CHC$_2$H$_4$— | cyclopentyl | S |
| 16 | CH$_3$CH=CH(CH$_2$)$_3$— | CH$_3$CH=CH(CH$_2$)$_3$— | cyclopentyl | O |
| 17 | CH≡C— | CH≡C— | cyclopentyl | O |
| 18 | CH$_3$OCH$_2$— | CH$_3$OCH$_2$— | cyclopentyl | O |
| 19 | ClCH$_2$CH$_2$— | ClCH$_2$CH$_2$— | cyclopentyl | S |
| 20 | cyclopentyl | cyclopentyl | cyclopentyl | O |
| 21 | C$_2$H$_5$— | C$_2$H$_5$— | 1-methylcyclopentyl | O |

What is claimed is:

1. A compound of the formula:

$$\begin{array}{c} H \\ | \\ X \\ \| \\ RR^1NC-N \end{array} \diagup \begin{array}{c} C=N \\ | \\ N=CSO_2(CH_2)_nR^2 \end{array}$$

wherein X is O or S; R and R$^1$ are substituted or unsubstituted (C$_1$-C$_6$)alkyl, (C$_2$-C$_6$)alkenyl, (C$_2$-C$_6$)alkynyl or (C$_3$-C$_6$)cycloalkyl wherein the substituent may be lower alkoxy or halo, or when R or R$^1$ are substituted (C$_3$-C$_6$)cycloalkyl the substituent may be lower alkyl, lower alkenyl or lower alkynyl; R$^2$ is substituted or unsubstituted (C$_3$-C$_9$)cycloalkyl wherein the substituent is selected from lower alkyl, lower alkenyl, lower alkynyl, lower alkoxy, lower alkoxyalkyl or halo; and n is 0, 1 or 2.

2. The compound of claim 1 of the formula:

$$\begin{array}{c} O \\ \| \\ C-NR^3R^4 \\ | \\ N \diagdown N \\ \| \\ N \underline{\hspace{1em}} SO_2CH_2R^5 \end{array}$$

wherein R$^3$ and R$^4$ are the same or different (C$_1$-C$_6$)alkyl or (C$_2$-C$_6$)alkenyl radicals and R$^5$ is cycloalkyl of from 3 to 7 nuclear carbon atoms.

3. The compound of claim 2 wherein R$^3$ and R$^4$ are the same or different (C$_1$-C$_3$)alkyl and R$^5$ is cycloalkyl of from 5 to 7 nuclear carbon atoms.

4. The compound of claim 3 named 3-(cyclopentylmethylsulfonyl)-N,N-diethyl-1,2,4-triazole-1-carboxamide.

5. The compound of claim 3 named 3-(cyclohexylmethylsulfonyl)-N,N-diethyl-1,2,4-triazole-1-carboxamide.

6. The compound of claim 2 named 3-(cyclohexylmethylsulfonyl)-N,N-diallyl-1,2,4-triazole-1-carboxamide.

7. The compound of claim 3 named 3-(cycloheptylmethylsulfonyl)-N,N-diethyl-1,2,4-triazole-1-carboxamide.

8. The compound of claim 2 named 3-(cyclopropylmethylsulfonyl)-N,N-diethyl-1,2,4-triazole-1-carboxamide.

9. The compound of claim 2 named 3-(cyclobutylmethylsulfonyl)-N,N-diethyl-1,2,4-triazole-1-carboxamide.

10. A herbicidal composition which comprises as an active ingredient a herbicidally effective amount of a compound of claim 1 in association with a carrier or diluent.

11. A herbicidal composition which comprises as an active ingredient a herbicidally effective amount of a compound of claim 2 in association with a carrier or diluent.

12. A herbicidal composition which comprises as an active ingredient a herbicidally effective amount of a compound of claim 3 in association with a carrier or diluent.

13. A herbicidal composition which comprises as an active ingredient a herbicidally effective amount of the compound of claim 5 in association with a carrier or diluent.

* * * * *